US009689870B2

(12) United States Patent
Ding

(10) Patent No.: US 9,689,870 B2
(45) Date of Patent: Jun. 27, 2017

(54) ASSAY DEVICE HAVING MULTIPLE REAGENT CELLS

(71) Applicant: Ortho-Clinical Diagnostics, Inc., Raritan, NJ (US)

(72) Inventor: Zhong Ding, Pittsford, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 0 days.

(21) Appl. No.: 14/578,745

(22) Filed: Dec. 22, 2014

(65) Prior Publication Data

US 2016/0178623 A1    Jun. 23, 2016

Related U.S. Application Data

(63) Continuation of application No. 13/744,442, filed on Jan. 18, 2013, now abandoned.
(Continued)

(51) Int. Cl.
*G01N 33/52* (2006.01)
*G01N 33/543* (2006.01)
(Continued)

(52) U.S. Cl.
CPC ... *G01N 33/54386* (2013.01); *G01N 33/5302* (2013.01); *G01N 33/54393* (2013.01); *G01N 33/558* (2013.01)

(58) Field of Classification Search
CPC ....... G01N 33/54386; G01N 33/54393; G01N 33/558; G01N 33/5302
See application file for complete search history.

(56) References Cited

U.S. PATENT DOCUMENTS 5,120,643 A    6/1992    Ching et al.
5,503,985 A    4/1996    Cathey et al.
(Continued)

FOREIGN PATENT DOCUMENTS

EP    1120164 A2    8/2001
EP    2031376 A2    3/2009
(Continued)

OTHER PUBLICATIONS

European Search Report—Mar. 25, 2013—EP13 151 781.5.
(Continued)

*Primary Examiner* — Dennis M White
(74) *Attorney, Agent, or Firm* — Barclay Damon, LLP

(57) ABSTRACT

An assay device includes: a liquid sample zone; a reagent zone downstream and in fluid communication with the sample zone. The reagent zone includes at least two reagent cells containing a reagent material and arranged in the reagent zone such that each reagent cell experiences substantially the same flow conditions of sample from the sample zone. The reagent cells divide the sample flow from the sample zone into multiple flow streams. Also includes are: one or more flow control elements disposed downstream from the reagent zone which combine the multiple flow streams into fewer flow streams; a detection zone in fluid communication with the reagent zone; and a wicking zone in fluid communication with the detection zone having a capacity to receive liquid sample flowing from the detection zone. The sample addition zone, the detection zone and the wicking zone define a fluid flow path.

23 Claims, 16 Drawing Sheets

Related U.S. Application Data

(60) Provisional application No. 61/588,738, filed on Jan. 20, 2012.

(51) Int. Cl.
  *G01N 33/558* (2006.01)
  *G01N 33/53* (2006.01)

(56) References Cited

U.S. PATENT DOCUMENTS

| | | |
|---|---|---|
| 5,559,041 A | 9/1996 | Kang et al. |
| 5,637,469 A * | 6/1997 | Wilding ............... B01J 19/0093 366/DIG. 3 |
| 5,714,389 A | 2/1998 | Charlton et al. |
| 6,139,800 A | 10/2000 | Chandler |
| 6,203,757 B1 | 3/2001 | Lu et al. |
| 6,228,660 B1 | 5/2001 | May et al. |
| 6,270,641 B1 | 8/2001 | Griffiths et al. |
| 6,271,040 B1 | 8/2001 | Buechler |
| 6,372,542 B1 | 4/2002 | Martin et al. |
| 6,733,682 B1 | 5/2004 | Björkman et al. |
| 6,811,736 B1 | 11/2004 | Ohman et al. |
| 6,884,370 B2 | 4/2005 | Öhman et al. |
| 7,204,139 B2 | 4/2007 | Takayama |
| 7,416,700 B2 | 8/2008 | Buechler et al. |
| 7,687,031 B2 | 3/2010 | Yamagata et al. |
| 8,288,151 B2 | 10/2012 | Aoyagi |
| 2005/0026346 A1 | 2/2005 | Blankenstein |
| 2005/0042766 A1 | 2/2005 | Ohman et al. |
| 2006/0216195 A1 | 9/2006 | Blankenstein et al. |
| 2006/0239859 A1 | 10/2006 | Ohman et al. |
| 2006/0285996 A1 | 12/2006 | Ohman et al. |
| 2006/0289787 A1 | 12/2006 | Ohman et al. |
| 2007/0042499 A1 | 2/2007 | Schwind et al. |
| 2007/0105236 A1 | 5/2007 | Chang et al. |
| 2007/0231883 A1 | 10/2007 | Lindstrom et al. |
| 2009/0111197 A1 * | 4/2009 | Khan ................. B01L 3/502746 436/536 |
| 2009/0311805 A1 | 12/2009 | Bergman et al. |
| 2010/0009430 A1 * | 1/2010 | Wan .................. B01L 3/502746 435/287.1 |
| 2010/0041571 A1 | 2/2010 | Cohen et al. |

FOREIGN PATENT DOCUMENTS

| | | |
|---|---|---|
| EP | 2 135 676 A1 | 12/2009 |
| GB | 2469071 A | 10/2010 |
| JP | 2002-243734 | 8/2002 |
| JP | 2004-93558 | 3/2004 |
| JP | 2006-208388 | 8/2006 |
| JP | 2007-40969 | 2/2007 |
| JP | 2008-547017 | 12/2008 |
| JP | 2010-14709 | 1/2010 |
| JP | 2011-523061 | 8/2011 |
| WO | WO 90/11519 A1 | 10/1990 |
| WO | WO 03/048736 A2 | 6/2003 |
| WO | WO 03/103835 A1 | 12/2003 |
| WO | WO 2005/089082 A2 | 9/2005 |
| WO | WO 2005/118139 A1 | 12/2005 |
| WO | WO 2006/137785 A1 | 12/2006 |
| WO | WO 2007/012975 A1 | 2/2007 |
| WO | WO 2007/149042 A1 | 12/2007 |
| WO | WO 2008/122796 A1 | 10/2008 |
| WO | WO 2009/149362 A2 | 12/2009 |

OTHER PUBLICATIONS

Japanese Office Action for JP 2013-007008; dated Nov. 8, 2016; 4 pages.

Japanese Office Action for JP 2013-007008; dated Feb. 28, 2017; 4 pages.

* cited by examiner

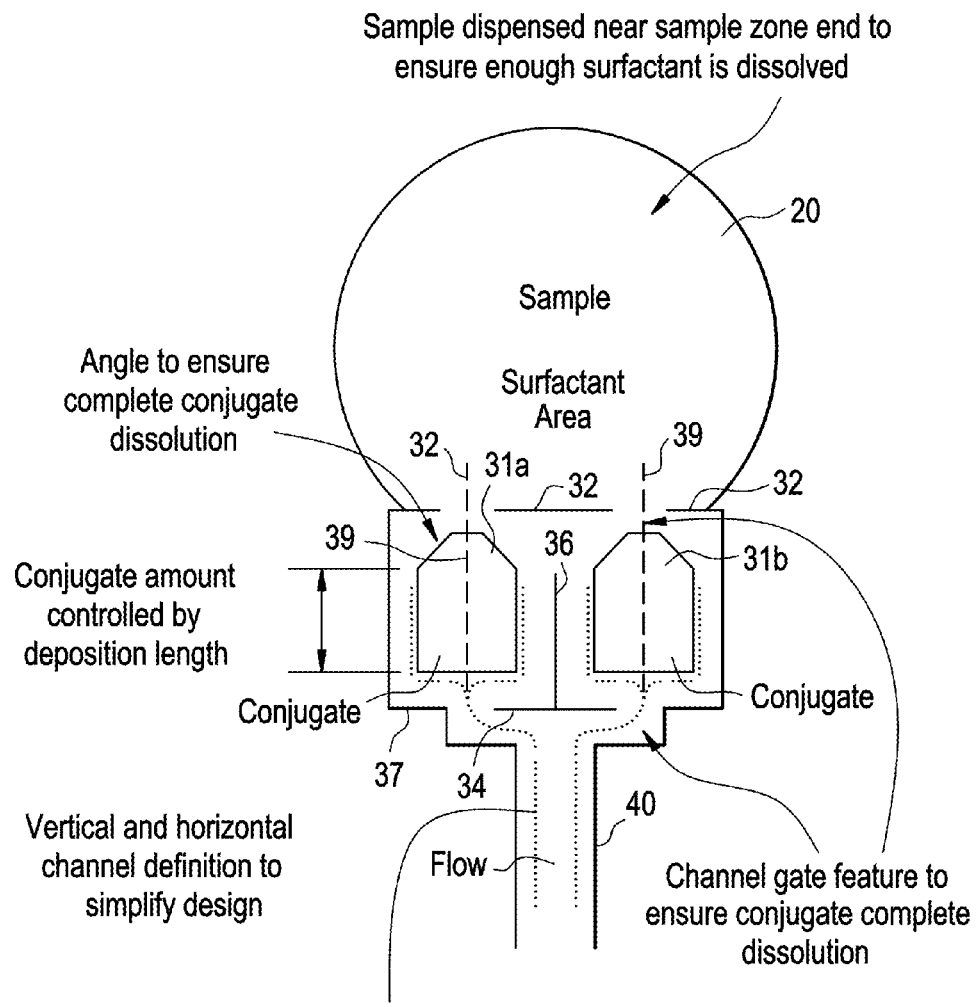

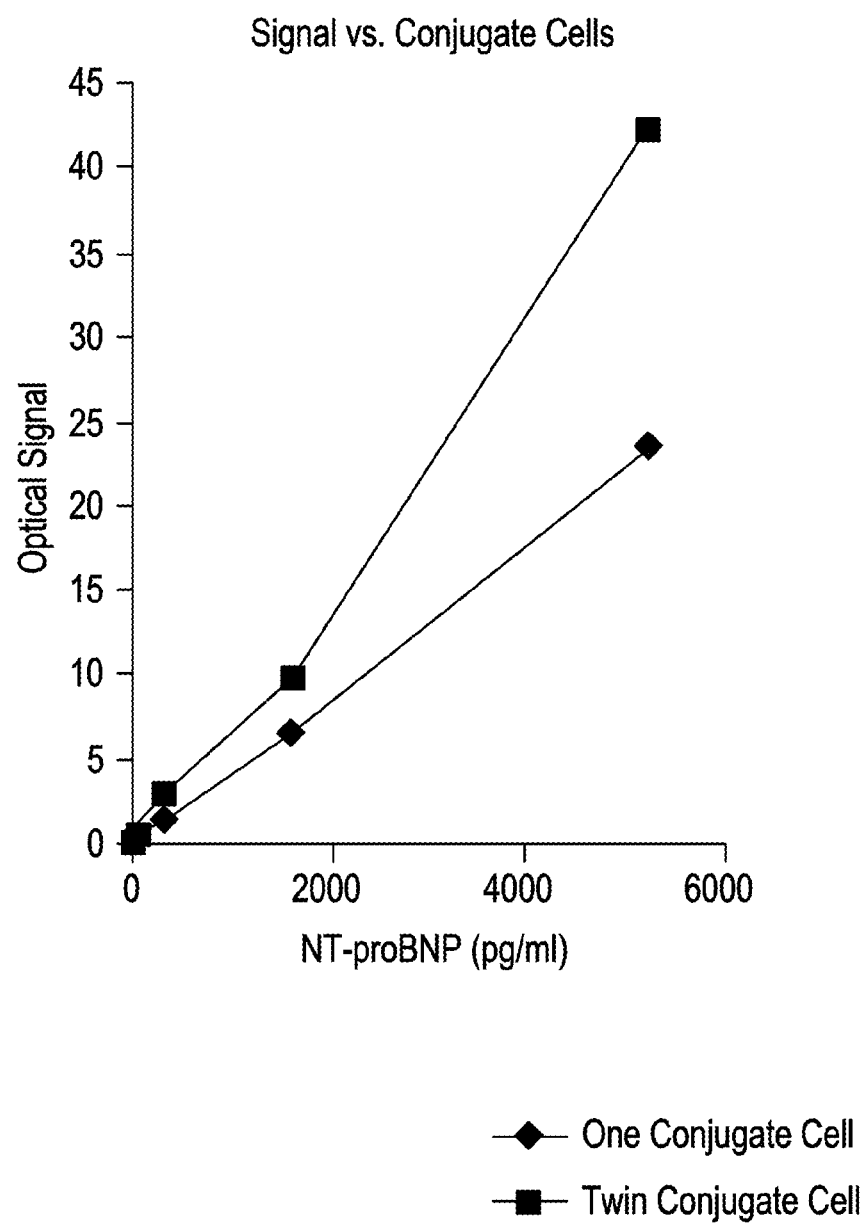

ASSAY DEVICE HAVING MULTIPLE REAGENT CELLS

CROSS REFERENCE TO RELATED APPLICATIONS

This patent application is a continuation of and which claims priority to U.S. Non-Provisional application Ser. No. 13/744,442, filed Jan. 18, 2013 which also claims benefit of U.S. Provisional Application No. 61/588,738, filed Jan. 20, 2012, the disclosures of which are incorporated by reference in their entireties.

FIELD OF THE INVENTION

The present invention relates to the field of diagnostic assays, and in particular to lateral flow assays where an analyte to be detected is present in a biological sample.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture. Understandably it is difficult to meet all these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120, 643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

WO 2007/012975 discloses a hybrid device that includes a capillary channel having bifurcations that is stated to help present a more united fluid front to the resuspension chamber, and thereby increase the speed of detection of a substance and improve the accuracy of detected results. US 2009/0311805 discloses an assay device having deposited conjugate in a conjugate zone. U.S. Pat. No. 6,271,040 discloses an assay device having a reaction chamber 4 that includes dried or lyophilized powders. The shape of the reaction chamber is disclosed as being such that the movement of the reaction mixtures from the reaction chamber is not turbulent and eddies are not formed as a result of the movement out of the reaction chamber.

Another type of assay devices is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

A known non-porous assay device is shown in FIG. 1. The assay device 1, has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay. Unbound dissolved conjugate material will be swept past the detection zone into the at least one wicking zone 5.

An instrument such as that disclosed in US 20060289787A1, US20070231883A1, U.S. Pat. No. 7,416, 700 and U.S. Pat. No. 6,139,800 all incorporated by reference in their entireties is able to detect the bound conjugated analyte and label in the reaction zone. Common labels include fluorescent dyes that can be detected by instruments which excite the fluorescent dyes and incorporate a detector capable of detecting the fluorescent dyes. Such instruments have a read window that has a width that is typically on the order of 1 mm, which is a generally sufficient width to read enough signal, subject to an adequate width of the conjugate plume.

One drawback with such known assay devices such as those described above, is that the dissolved conjugate stream in the reaction zone is often narrower than the read window of the instrument, which may negatively impact assay sensitivity and variability. This is of particular concern for designs such as those described above where the conjugate material is deposited in the center of the conjugate zone and is dissolved from the sides as sample is flowing past. If the channel is made wider than the read window, although the dissolved reagent width may match the read window size, the fluid sample outside the read window contributes no signal and is wasted. Another drawback is that the dissolved reagent is not adequately mixed with the sample by the time it reaches the reaction zone, with the result being a lower signal in the middle of the reaction zone because dissolved reagent has local higher concentration and needs to diffuse to mix with sample further away from the reagent, and to bind with the analyte, and hence less signal being read by the read window of the instrument.

The sample size for such typical assay devices as shown in FIG. 1 are generally on the order of 200 µl. Such a sample size requires a venous blood draw from a medical professional such as a phlebotomist. There is an increasing need for lateral flow devices that are able to function with a much smaller sample size to accommodate the amount of blood available from a so-called "fingerstick" blood draw, which is on the order of 25 µl or less. Such a small amount of sample is the amount of blood in a drop of blood after pricking a finger tip with a lancet. Home blood glucose meters typically use a drop of blood obtained in such a fashion to provide glucose levels in blood. Such a smaller sample size would not require a medical professional to draw the blood and would provide greater comfort to the patients providing the sample for analysis.

To reduce the sample size required, the dimensions of the lateral flow assay devices are reduced to accommodate the smaller sample size. However, it has been found that reducing the sample size and dimensions of the device provides inadequate conjugate in the detection zone and accordingly less signal that can be read by the instrument. The inadequate conjugate in the detection zone is believed to be due to reduced sample size and inefficient use of the sample in the device, amongst other conditions. Another drawback of reducing dimensions is that the width of the detection zone will also be reduced, again making less signal available that can be read by the instrument.

Accordingly, there is a need for an assay device that can provide a wider reagent plume in the detection zone, better mix the dissolved reagent and sample, and make more efficient use of sample in an assay device, particularly in those devices where the conjugate material is deposited in the center of the conjugate zone and is dissolved from the sides.

SUMMARY OF THE INVENTION

The present invention is directed to an assay device that alleviates one or more the foregoing problems described above.

One aspect of the invention is directed to an assay device that includes: a liquid sample zone; a reagent zone downstream and in fluid communication with the sample zone comprising at least two reagent cells containing a reagent material and arranged in the reagent zone such that each reagent cell experiences substantially the same flow conditions of sample from the sample zone, wherein the reagent cells divide the sample flow from the sample zone into multiple flow streams; one or more flow control elements disposed downstream from the reagent zone which combine the multiple flow streams into fewer flow streams; a detection zone in fluid communication with the reagent zone; and a wicking zone in fluid communication with the detection zone having a capacity to receive liquid sample flowing from the detection zone, wherein the sample addition zone, the detection zone and the wicking zone define a fluid flow path.

Another aspect of the invention is directed to an assay device that includes: a liquid sample addition zone; a reagent zone downstream and in fluid communication with the sample addition zone comprising $2^n$ reagent cells, where n is a non-zero, non-negative integer, arranged in the reagent zone such that each reagent cell experiences substantially the same flow conditions of sample from the sample addition zone, wherein the reagent cells divide the sample flow from the sample addition zone into multiple flow streams; flow control elements which separate the reagent cells; one or more flow control elements disposed downstream from the reagent zone which combine the multiple flow streams into fewer flow streams; a detection zone in fluid communication with the reagent zone capable of producing a detectable signal; and a wicking zone in fluid communication with the capture zone having a capacity to receive liquid sample flowing from the capture zone, wherein the sample addition zone, the capture zone and the wicking zone define a fluid flow path.

According to another aspect of the invention, there has been provided a method of performing an assay on a liquid sample for the presence or concentration of one or more analyte(s) or control(s), on the assay device described above. The method includes: depositing a liquid sample containing the analyte(s) of interest onto a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analyte(s) or control(s).

According to another aspect of the invention, there has been provided a method of controlling the flow around the reagent zone in an assay device. The method includes: providing a liquid sample zone; providing a reagent zone upstream and in fluid communication with the sample zone comprising at least two reagent cells arranged in the reagent zone such that each reagent cell experiences substantially the same flow conditions of sample from the sample zone, wherein the reagent cells divide the sample flow from the sample zone into multiple flow streams; providing one or more flow control elements disposed upstream from the reagent zone, arranged to provide channel gates having a width narrower than the reagent cells and which are adapted to constrict the flow from the sample leaving the sample zone; providing one or more flow control elements disposed downstream from the reagent zone which combine the multiple flow streams into fewer flow streams; providing a detection zone in fluid communication with the reagent zone; providing a wicking zone in fluid communication with the capture zone having a capacity to receive liquid sample flowing from the capture zone, wherein the sample zone, the detection zone and the wicking zone define a fluid flow path; adding sample to the sample zone; flowing the sample from the sample zone through the upstream flow channel gates which increase the velocity of the flow; flowing the sample past the reagent zone, whereby the flow has an increased velocity next to the reagent boundary compared to the flow at a distance from the reagent boundary, resulting in a more complete dissolution of the reagent zone; flowing the sample past the downstream flow channel gates, which increases the velocity of the flow and results in a wider reagent plume flowing through the detection zone, as compared to a reagent plume generated by a single reagent cell.

Further objects, features and advantages of the present invention will be apparent to those skilled in the art from detailed consideration of the preferred embodiments that follow.

BRIEF DESCRIPTION OF THE DRAWINGS

FIG. 9 shows a graph of signal strength versus the number of reagent (i.e., conjugate) cells

DETAILED DESCRIPTION OF PREFERRED EMBODIMENTS

Figure 1:
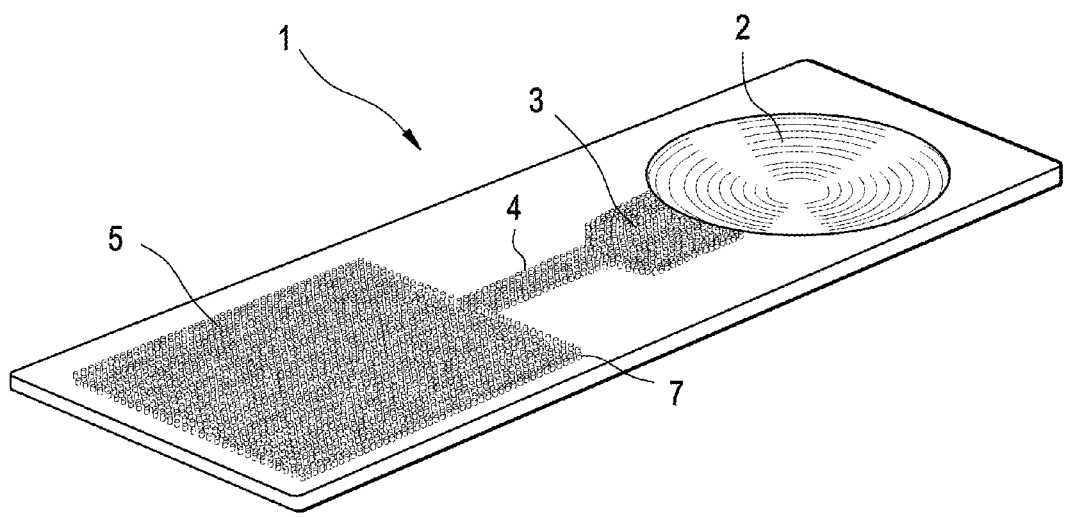
FIG. 1 shows a known assay device.

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

In the present invention, the determination based on lateral flow of a sample and the interaction of components present in the sample with reagents present in the device or added to the device during the procedure and detection of such interaction, either qualitatively or quantitatively, may be for any purpose, such as diagnostic purposes. Such tests are often referred to as lateral flow assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The terms "zone", "area" and "site" are used in the context of this description, examples and claims to define parts of the fluid flow path on a substrate, either in prior art devices or in a device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

Figure 2:
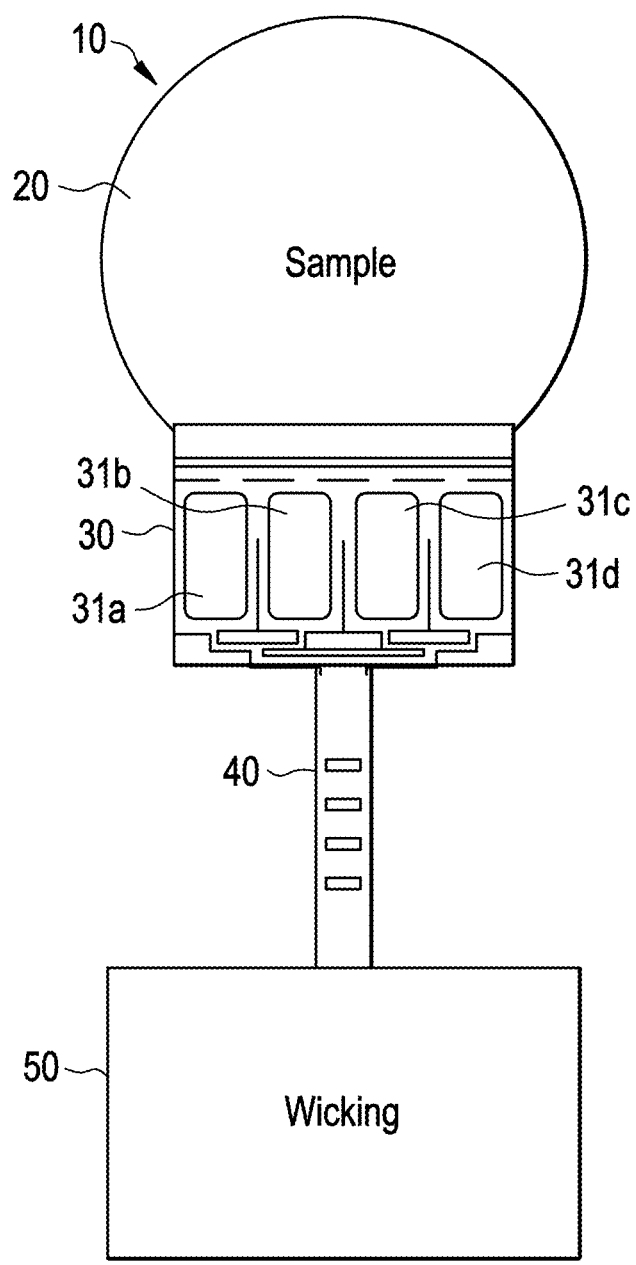
FIG. 2 shows a schematic view of an assay device having four reagent cells according to an embodiment of the invention.

The present invention is directed to a lateral flow assay device for determining the presence or amount of at least one analyte that solves, at least in part, the problem of lowered signal due to a narrow reagent plume or reduced sample size. FIG. 2 shows a schematic view of a preferred embodiment of such a device according to the invention. The assay device 10 has at least one sample zone (also referred to as sample addition zone) 20, at least one reagent zone 30, at least one detection zone 40, and at least one wicking zone 50. The zones form a flow path by which sample flows from the sample addition zone to the wicking zone.

Components of the assay device (i.e., a physical structure of the device whether or not a discrete piece from other parts of the device) can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 1 shows projections 7.

In one embodiment the flow path is at least partially open. In another embodiment the flow path is entirely open. Open means that there is no lid or cover at a capillary distance. Thus the lid, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 μm, preferably about 30 to about 100 μm, a diameter of about 10 to about 160 μm, preferably 40 to about 100 μm, and a gap or gaps between the projections of about 3 to about 200 μm, preferably 5 to about 50 μm or 10 to 50 μm from each other. The flow channel may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone 20, also referred to as the liquid sample addition zone, receives sample from a sample dispenser, such as a pipette. The sample is typically deposited onto the top of the zone. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 1. In those devices that can use finger stick volumes of blood, the sample can be directly touched off from the finger, or by a capillary pipette such as described in co pending application.

A filter material (not shown) can be placed in the sample addition zone to filter particulates from the sample or to filter blood cells from blood so that plasma can travel further through the device.

Located between the sample addition zone and the detection zone is a reagent zone 30. The reagent zone can include reagent(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. The amount of reagent in the reagent zone can be adjusted by the length of reagent deposited into the device while maintaining the same reagent width. The amount of reagent can also be adjusted by changing the width while maintaining the length. The amount of reagent can further be adjusted by changing both width and length simultaneously. In one preferred embodiment, the reagent zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}I$ and $^{32}P$.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in an "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 60 in FIG. 6. The reagent addition zone can allow addition of a reagent externally from the device. For example, the reagent addition zone may be used to add an interrupting reagent that may be used to wash the sample and other unbound components present in the fluid flow path by the wicking zone. In a preferred embodiment the reagent addition zone 60 is located after the reagent zone 30.

Downstream from the liquid sample zone and the reagent zone is the detection zone 40 which is in fluid communication with the sample addition zone. The detection zone 40 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in co pending application entitled "Low Volume Assay Device Having Increased Sensitivity" (Application No. 61/588,788) filed Jan. 20, 2012 and incorporated by reference in its entirety, are significantly narrower, e.g., 1.5 mm or less.

The detection zone is where any detectable signal is read. In a preferred embodiment attached to the projections in the detection zone are capture elements. The capture elements can include binding partners for the conjugate or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the detection zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the detection zone or those added through the reagent addition zone. The reagent plume can include the conjugate having both the detection element and binding partner, in which case it is often referred to as a conjugate plume. As noted throughout, one challenge facing the inventors was to keep the reagent plume as wide as possible as it enters the detection zone.

The present invention is based, in part, on the surprising discovery that an assay device such as those described herein which employs multiple areas having reagent material (hereinafter referred to as "reagent cells") in a reagent zone along with elements to recombine multiple flow streams that result from the multiple reagent cells into one flow stream will result in a more desirably mixed, wider reagent plume as it leaves the reagent zone and enters the detection zone.

Figure 3:
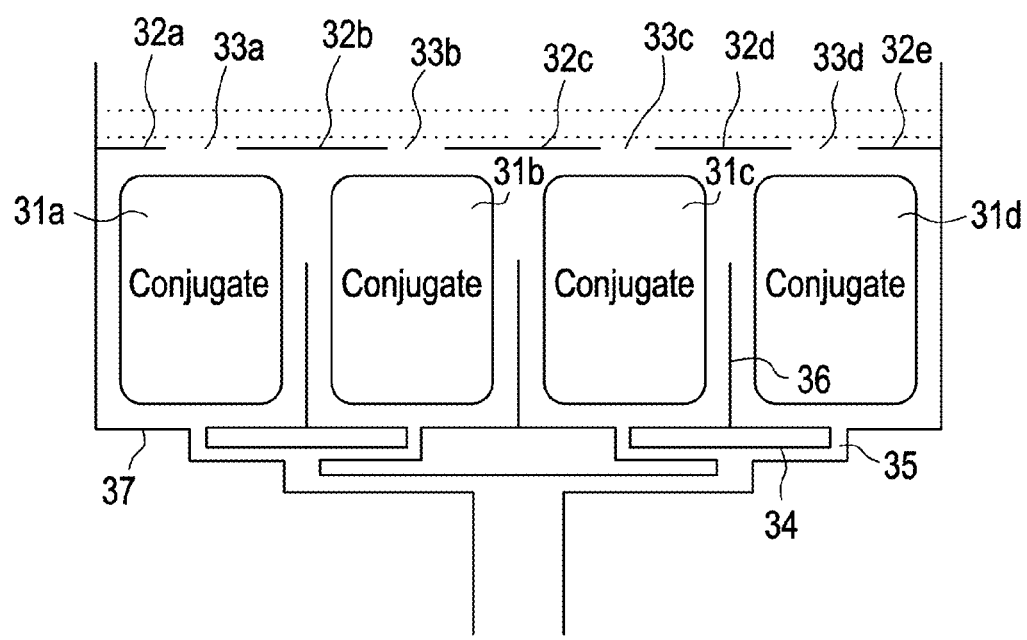
FIG. 3 shows an expanded view of the reagent zone according to FIG. 2.

In one preferred embodiment shown in FIG. 2 and in more detail in FIG. 3 multiple and preferably identical reagent cells, i.e., greater than two cells (4 cells in the case of FIGS. 2 and 3) are arranged in a way such that each one reagent cell experiences the same flow conditions due to the symmetry of the geometry of the cells in the reagent zone. The dissolved reagents from each reagent cell flows through channel gates formed by flow control elements, and merge to form a single stream as it flows to the detection zone.

Figure 4:
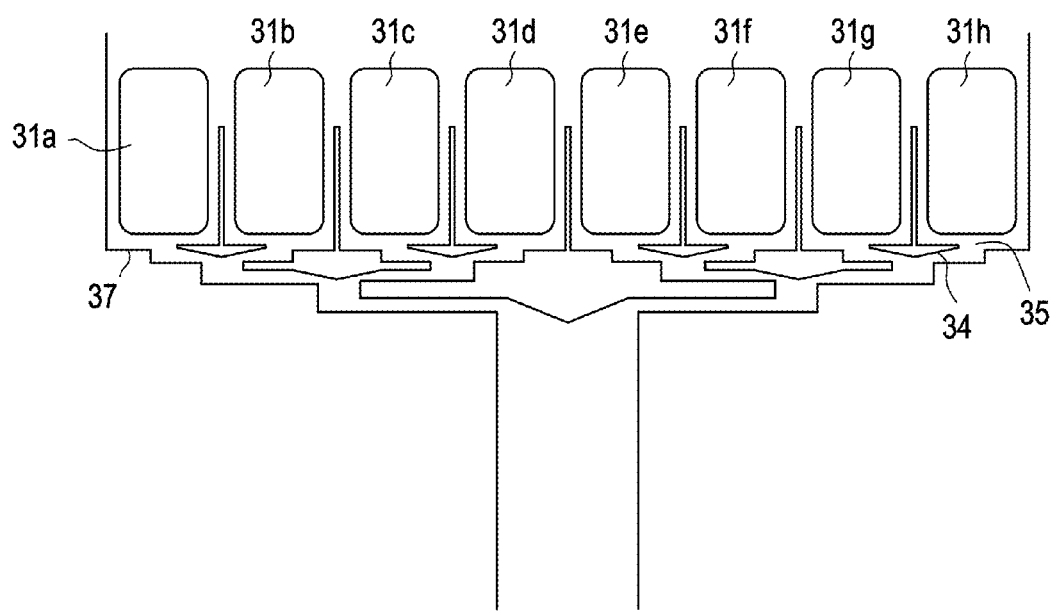
FIG. 4 shows a schematic view of a reagent zone of an assay device having eight reagent cells according to a preferred embodiment of the invention.

More specifically FIGS. 2 and 3 show an embodiment that contains four reagent cells 31*a-d*. FIG. 4 shows an embodiment that contains eight reagent cells 31*a-h*. The reagent cells are symmetrically arranged in the reagent zone, such that each will experience identical flow conditions of sample as the sample stream passes out of the sample addition zone into the reagent zone. While any number of conjugate cells two or greater (e.g., 3, 4, 5, 6, 7, etc.) are within the scope of the present invention, it is preferred to have an geometric progression of cells represented by the formula, $2^n$ reagent cells, where n is a non-zero, non-negative integer. Thus, the number of cells in this preferred embodiment would be 2, 4, 8, 16, etc. reagent cells. For example, for 8 cells, n would be 3 and for 16 cells, n would be 4, etc.

Located downstream from the reagent zone are downstream flow control elements 34 and flow channel gates 35 (i.e. openings), which are arranged to combine the multiple streams coming off of the reagent cells back into a single stream for transport to the detection zone. The downstream flow control elements combine the multiple streams into a smaller number of streams until a single flow stream is achieved.

In a preferred embodiment, flow control elements 34 will have a portion 36 that extends between each of the reagent cells in the direction of fluid flow as shown in FIG. 3. In this embodiment, $2^n$ reagent cells will result in $(2^n) \times 2$ flow streams. A first stage set of flow control elements will define $2^n$ first stage of flow control gates 35 immediately downstream of the reagent cell and centered along the axis of symmetry of the reagent cell in the direction of flow. Exiting the first stage of flow control gates will be $2^n$ flow streams. A second stage of flow control elements will define $2^{(n-1)}$ flow control gates, which results in $2^{(n-1)}$ flow streams, and so on until a single flow stream results. The resulting single flow stream will have a wider reagent plume than would have been possible with known lateral flow devices, resulting in more signal.

The flow control elements can be any structure that redirects flow either before or after the reagent cells. They can be structures protruding from the substrate of the assay device and are formed in the same manner as the micro posts described above. Some of the structures can be sidewalls of the flow channels where the flow channels narrow as shown by reference numeral 37 in FIGS. 3, 6, 7 and 15.

In a preferred embodiment, structures are provided prior to the reagent cells to provide uniform flow across the entire width of the flow path to achieve uniform flow to each of the reagent cells. For example, larger spacings between the pillars in a direction perpendicular to flow in the area upstream of the reagent cells provides a more uniform flow across the width of the flow path.

In a particularly preferred embodiment, each reagent cell includes upstream flow control elements 32 which are placed between the sample addition zone and the reagent zone to define flow channel gates 33. The fluid inlet and outlet locations provided by the upstream and downstream channel gates, respectively, are preferably selected to ensure the streamline, i.e., the path the fluid flows, from the inlet to the outlet to be the shortest at the interface between the undissolved reagent and the sample fluid. This will ensure a more complete dissolution of the reagent. Some of the structures can be sidewalls of the flow channels where the flow channels narrow as shown by reference numeral 38 in FIGS. 3, 6, 7 and 15.

Preferably, each reagent cell is separated from the other reagent cell by a reagent cell separator 36 that extends between the reagent cell, preferably from the downstream flow control element up to the upstream flow control element as shown in FIGS. 2-7. The width for either inlet or outlet is smaller than the width of the cell itself. This feature allows fluid to flow much faster near the reagent boundary, and flow slower further away from the deposited reagent. This effect contributes to the complete dissolution of the reagent. It also makes the dissolved reagent plume wider. In a preferred embodiment, the reagent cell width is about 3 to 6 mm, and the inlet and outlet width is less than or equal to 0.5 mm. A wider inlet and outlet will generate to a narrower plume, which is not desirable for the reasons described above.

Figure 5A:
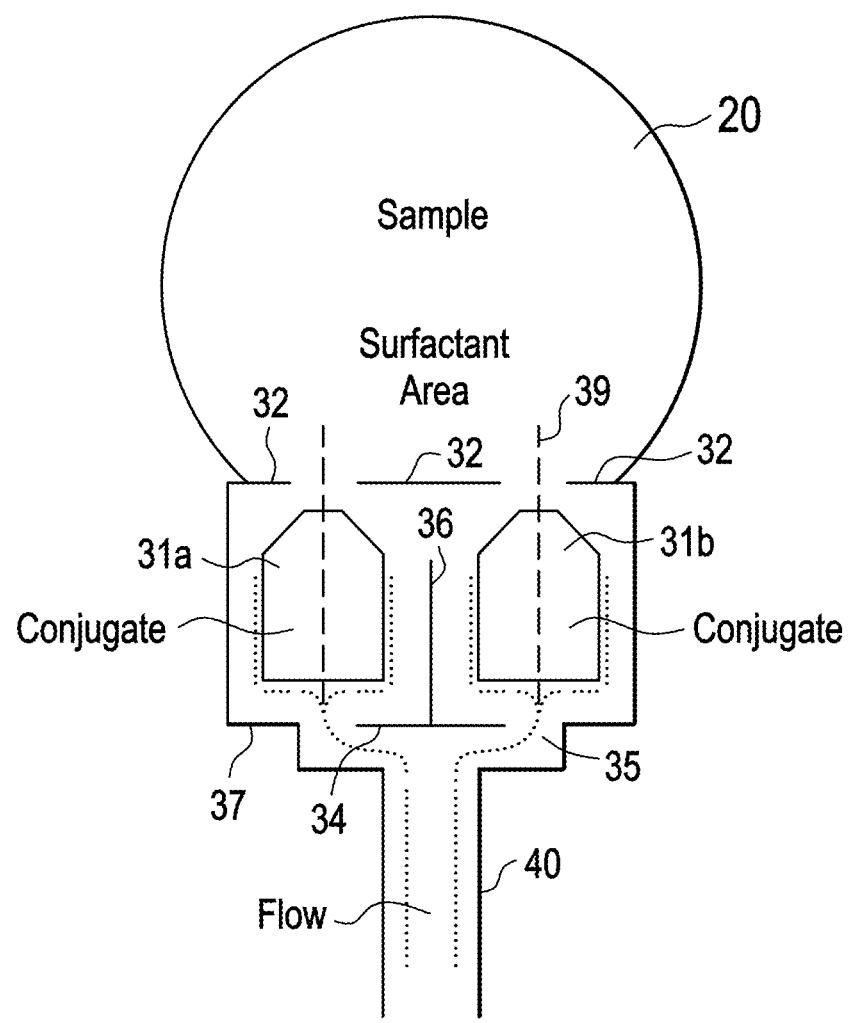
FIGS. 5a and b show schematic views of an assay device having two reagent cells according to a preferred embodiment of the invention.

For this embodiment, it is important to maintain left and right symmetry as shown in FIGS. 5A and B for each individual reagent cell in the bifurcation design. The inlet and outlet of the flow channel gates are located along the line of symmetry 39 as shown in FIGS. 5A and B to ensure flow symmetry inside the reagent cell and surrounding the deposited reagent. It is also important that the reagent cell lies in the line of symmetry 39 as show in FIGS. 5 A and B.

The deposited reagent material inside the line-symmetric reagent cell must also be left-right symmetric with the same line of symmetry of the reagent cell. This will contribute to reliably and completely dissolving the deposited reagent material.

In one embodiment multiple, separated reagent sub-cells are located within each reagent cell (not shown). Each of the reagent sub-cells should be symmetric with the same line of symmetry as the reagent cell itself.

Figure 6:
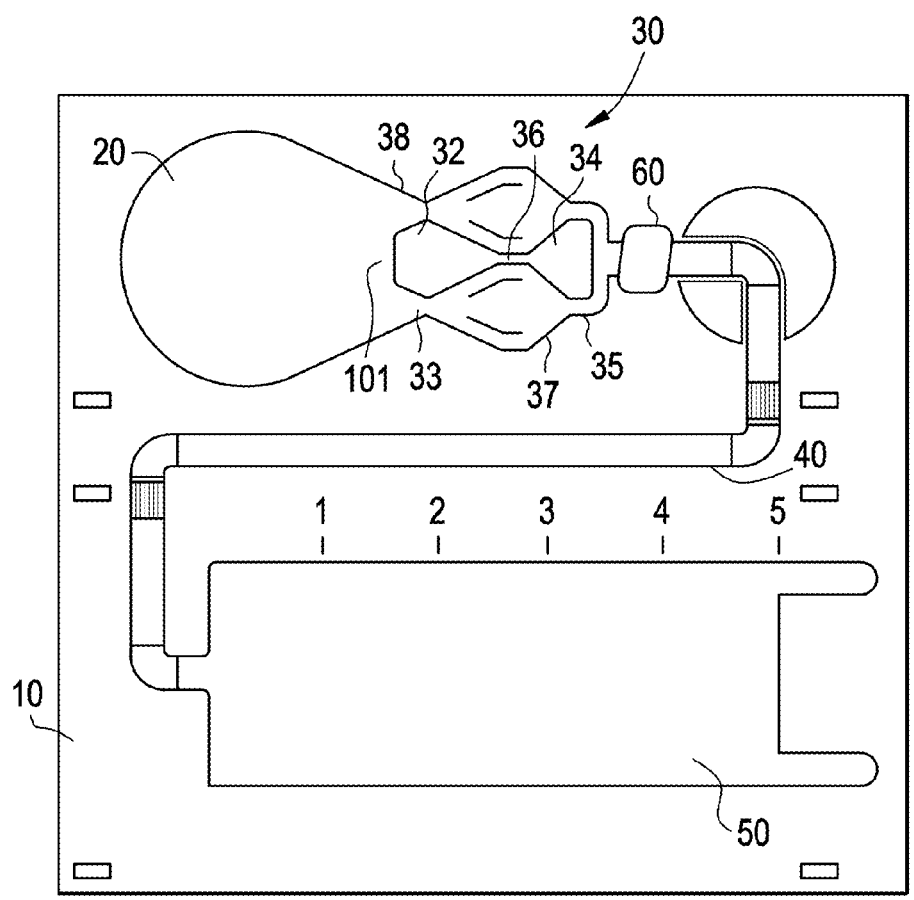
FIG. 6 shows a schematic view of an assay device having two reagent cells according to a preferred embodiment of the invention.
Figure 7:
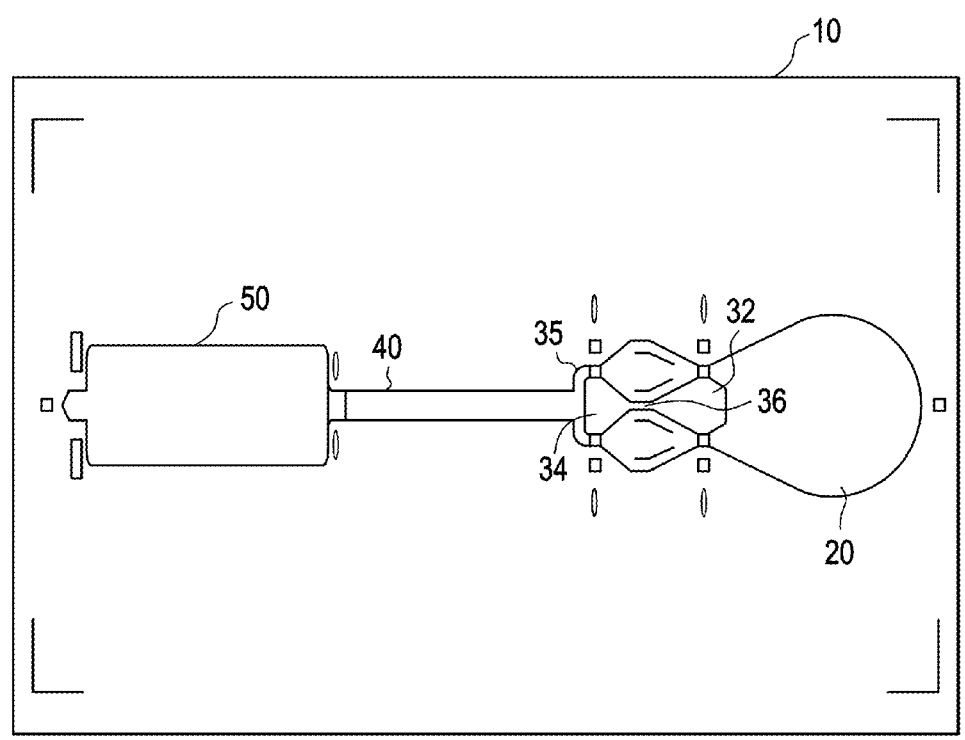
FIG. 7 shows a schematic view of an assay device having two reagent cells according to a preferred embodiment of the invention.
Figure 15:
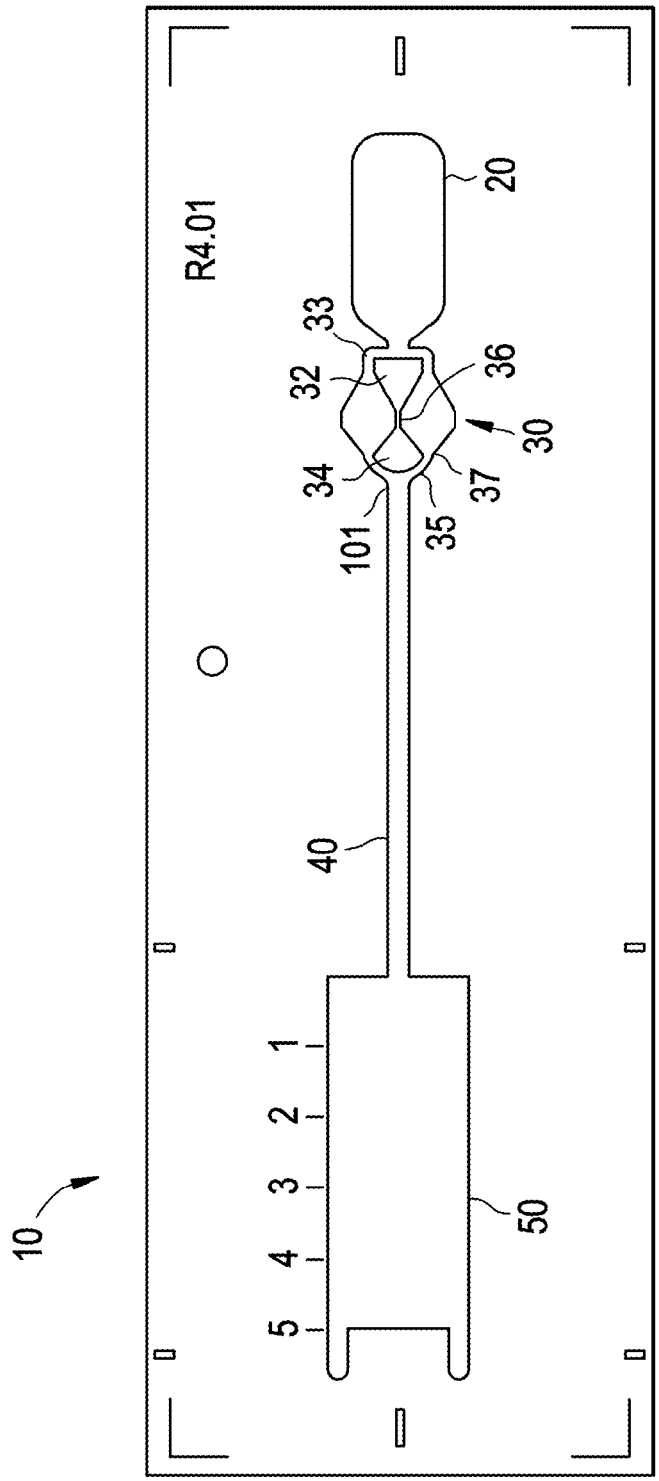
FIG. 15 shows a schematic view of an assay device having two reagent cells according to a preferred embodiment of the invention.

FIGS. 6, 7 and 15 show an assay device according to another embodiment of the invention having two reagent cells in the reagent zone. In the FIGS. 6, 7 and 15 embodiments, an hour glass shape structure 101 forms upstream 32 and downstream 34 flow control elements and upstream 33 and downstream 35 gates and reagent cell separator 36.

By using multiple reagent cells in the reagent zone, the width of the dissolved reagent plume entering the detection zone can be well defined and controlled by the number of reagent cells and the flow channels. The increased number of cells increases the width of the reagent stream. The much larger surface to volume ratio made possible by multiple reagent cells allows better reagent dissolution due to larger wetting area per unit volume, given the same flow rate. In addition, the flow rate at each cell can be lower while maintaining the overall flow rate at the desired level. For example, for a four reagent cell design, the flow rate past each of the reagent cell will be ¼ of the original flow rate entering the reagent cell. This provides more time for the sample to interact with the reagent material in the reagent cell, increasing dissolution of the reagent material into the sample flow.

Another advantage of the multiple reagent cell design is that the longer and narrower flow path with bends provided by the flow control elements, provides better mix by both diffusion and convection.

While the present invention, in particular the multiple reaction cells have been described with reference to non-porous projections, it is within the scope of the invention that the multiple reaction cells can be used on a nitrocellulose strip format or some other porous material. In one embodiment, the appropriate flow elements are formed via thermal means (i.e., melting the nitrocellulose with a heated die set forming the flow control elements) or with a printing technique where an insoluble barrier is laid down to form the flow paths and flow control elements.

Downstream from the detection zone is a wicking zone in fluid communication with the detection zone. The wicking zone is an area of the assay device with the capacity of receiving liquid sample and any other material in the flow path, e.g., unbound reagents, wash fluids, etc. The wicking zone provides a capillary force to continue moving the liquid sample through and out of the detection zone. The wicking zone can include a porous material such as nitrocellulose or can be a non-porous structure such as the projections described herein. The wicking zone can also include non-capillary fluid driving means, such as using evaporative heating or a pump. Further details of wicking zones as used in assay devices according to the present invention can be found in patent publications US 2005/0042766 and US 2006/0239859, both of which are incorporated herein by reference in their entireties. Wicking zones are also described in co-pending patent application entitled "Controlling Fluid Flow Through An Assay Device" (Application No. 61/588,772), filed Jan. 20, 2012 and incorporated by reference in its entirety.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

In any of the above embodiments, the device is preferably a disposable assay device. The assay device may be contained in a housing for ease of handling and protection. If the assay device is contained in such a housing, the housing will preferably include a port for adding sample to the assay device.

The assay device of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

Another aspect of the invention is directed to a method of performing an assay on a liquid sample for the detection of one or more analytes of interest. A liquid sample containing the analyte(s) of interest is deposited onto the sample zone of the assay device, such as through a port in the housing of the device, or by touching off a finger directly onto the sample zone in the case of a fingerstick blood draw. The sample moves by capillary action through an optional filter, through upstream elements as described above, which increase the velocity of the flow, and into the reagent zone where it dissolves the reagent material where it may conjugated with a detection element, either directly or indirectly, such as through an antibody. The reagent zone includes at least two reagent cells containing the reagent material arranged in the reagent zone such that each reagent cell experiences substantially the same flow conditions of sample from the sample addition zone, preferably due to the symmetry of the reagent cell and the influence of the upstream elements. The sample flows through the reagent zone, with higher velocity next to the un-dissolved reagent boundary compared to the flow at a distance from the dry reagent boundary, resulting in a more complete dissolution of the reagent zone. As noted above, the increased velocity near the dry reagent is made possible by the elements, such as smaller inlet and outlet in the reagent zone The sample flows away from the reagent zone through downstream channel gates where it is recombined into a single flow having a wider dissolved reagent plume as in flows into the detection zone. In a preferred embodiment, the reagent plume will extend across the entire width of the detection zone.

Next the sample and reagent plume move by capillary action into the detection zone. There a signal representative of the presence or concentration of the analyte(s) or control is produced. In a preferred embodiment the sample or the one or more reagents having a detection element is captured having in the detection zone, such as by antibodies on the surface of the detection zone and a signal representative of the presence or concentration of the analyte(s) or control(s) is produced.

The reader as described above is then used to read the signal that is produced by the detection element to determine the presence or concentration of the analyte(s). The sample moves from the detection zone and into the wicking zone. The reader may read the signal immediately or a short time after the sample has moved through the detection zone. Also, one or more washes may follow the sample through the device to wash any unbound detection element away from the detection zone.

The method, assay device, and reader according to an embodiment of the invention have many advantages, mainly related to the improved detection kinetics of the immunochemical reactions and the increased sensitivity of the assay.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Figure 8A:
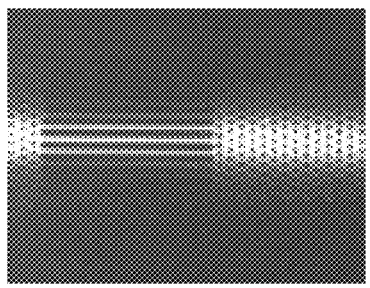
FIGS. 8A-D are photos showing the width of a reagent plume from a multiple reagent zone according to the present invention compared to a single reagent zone.
Figure 8C:
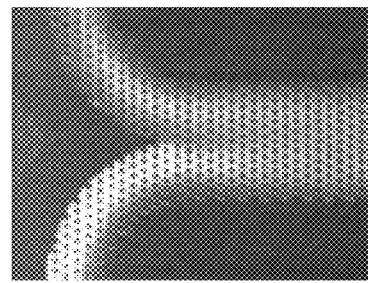
Figure 8B:
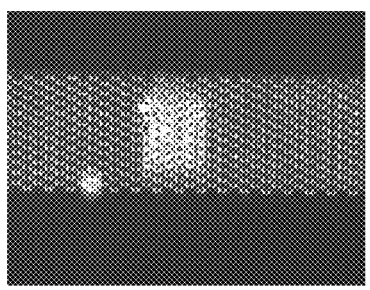
Figure 8D:
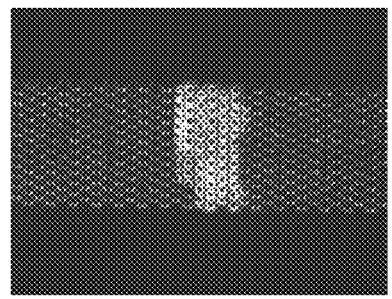

Assay devices made of Zeonor (Zeon, Japan) having oxidized dextran on the surface for covalently immobilization of proteins via Schiff base coupling were used. Fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. Sample was added to the sample zone of the device and the capillary action of the micropillar array distributed the sample through the flow channel into the wicking zone. A typical assay time was about 10 minutes. The signal intensities from the fluorescently labeled complexes in the detection zone were recorded in a prototype line-illuminating fluorescence scanner. FIG. 8A shows the width of the reagent plume using one reagent cells. FIG. 8B shows the width of the signal generated in the detection zone. FIG. 8C shows the width of the reagent plume using two reagent cells according to the present invention. FIGS. 8A and 8C clearly show the multiple reagent cells provides a significantly wider plume than a single reagent cell. FIGS. 8B and 8D show that the multiple reagent plume provides a wider signal generated in the detection zone which translates into more signal being read by the instrument.

Figure 10:
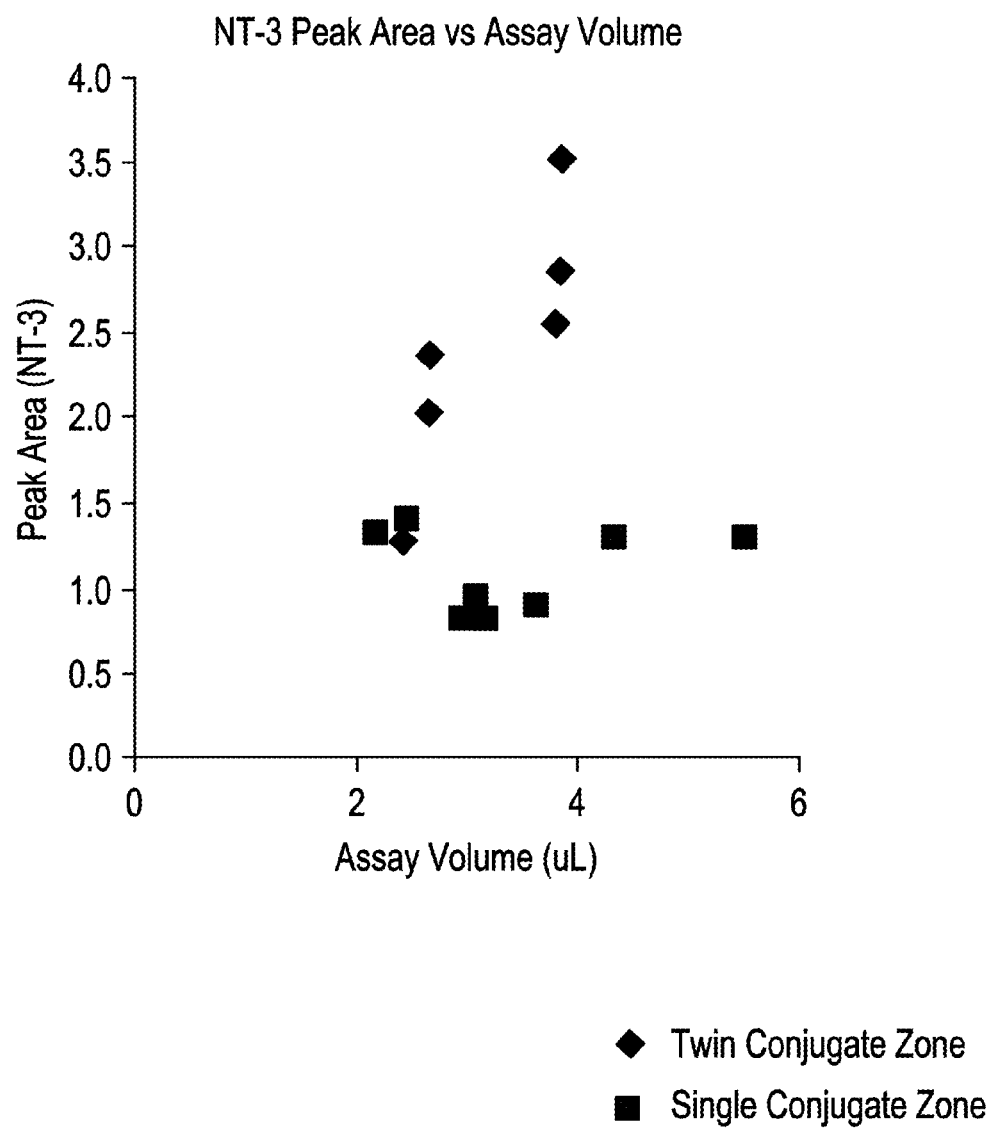
FIG. 10 shows a graph of peak are versus assay volume.

FIG. 9 shows a graph of signal strength versus the number of reagent (i.e., conjugate) cells. FIG. 10 shows a graph of peak are versus assay volume. FIGS. 9 and 10 both clearly demonstrate the superiority of multiple reagent cells vs. single reaction cells.

Example 2

Assay devices made of Zeonor (Zeon, Japan) having oxidized dextran on the surface for covalently immobilization of proteins via Schiff base coupling were used. Fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. Serum spiked with NT-proBNP was added to the sample zone of the device and the capillary action of the micropillar array distributed the sample through the flow channel into the wicking zone. Sample volumes of 15 microliters were employed on low-volume device designs R2.02, R2.04, R2.09 and R3.16. The R1.02 device design was a control device, intended for use with 200 microliters of whole blood, such as shown in FIG. 1. R1.02 devices were tested in this example with 45 microliters of serum. A typical assay time was about 10 minutes. The signal intensities from the fluorescently labeled complexes in the detection zone were recorded in a prototype line-illuminating fluorescence scanner.

Figure 11:
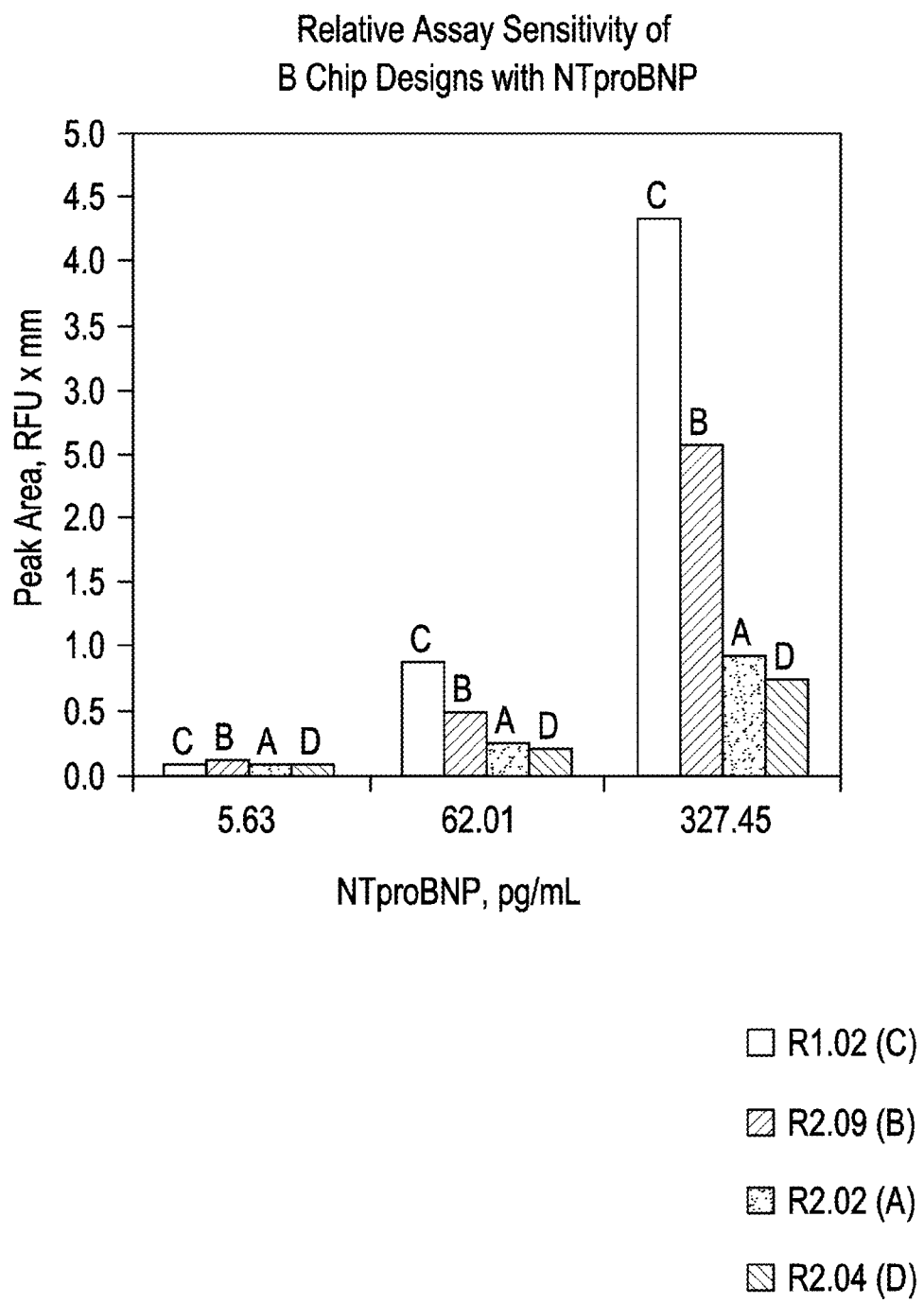
FIGS. 11 and 12 show sensitivity of different assay device designs with NTproBNP as the analyte.
Figure 12:
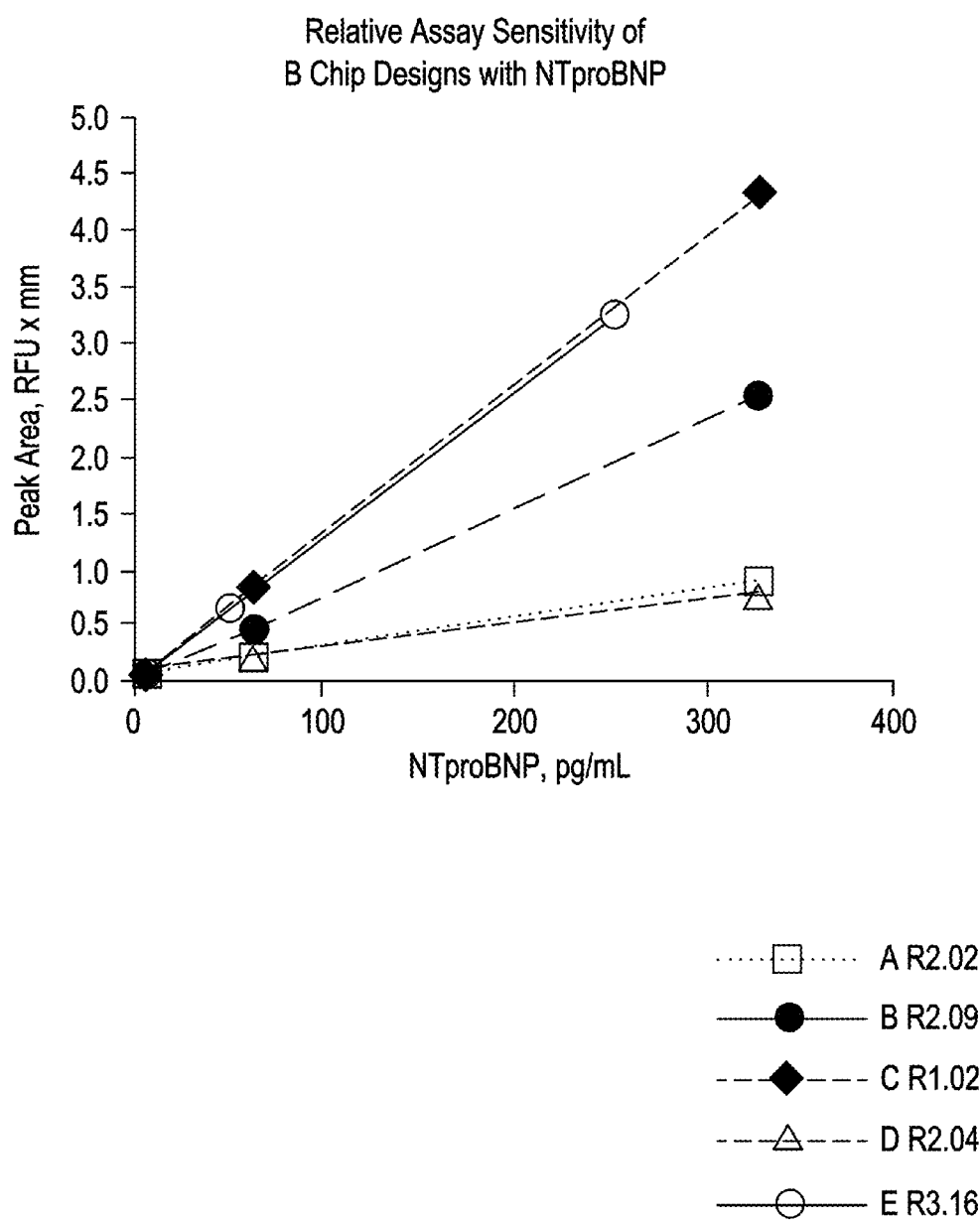

As shown in FIGS. 11 and 12, bar and curve A (R2.02) is a miniaturized device having a single-reagent cell and a directly scaled down detection zone having a detection zone width of 0.5 mm, whereas bar and curve B (R2.09) is a miniaturized device having dual reagent cell and a wider detection zone of 1 mm. Data for two additional device designs is also included for comparison. Curve and bar C (R1.02) is a conventionally sized assay device having a 200 uL whole blood sample volume, and curve and bar D (R2.04) is a single reagent cell device having a 1 mm detection zone width. Curve E (R3.16) includes dual reagent cells and a 1 mm wide detection zone. As the results show, the assay device represented by B having the multiple reagent cells according to the present invention has significantly improved sensitivity compared to other miniaturized designs. Even more significant is the assay device represented by E (also with multiple reagent cells) having a sensitivity that is equivalent to a conventionally sized device, which was unexpectedly surprising given the approximately 10× greater amount of sample that is available to generate signal in a conventional device.

Example 3

Figure 13:
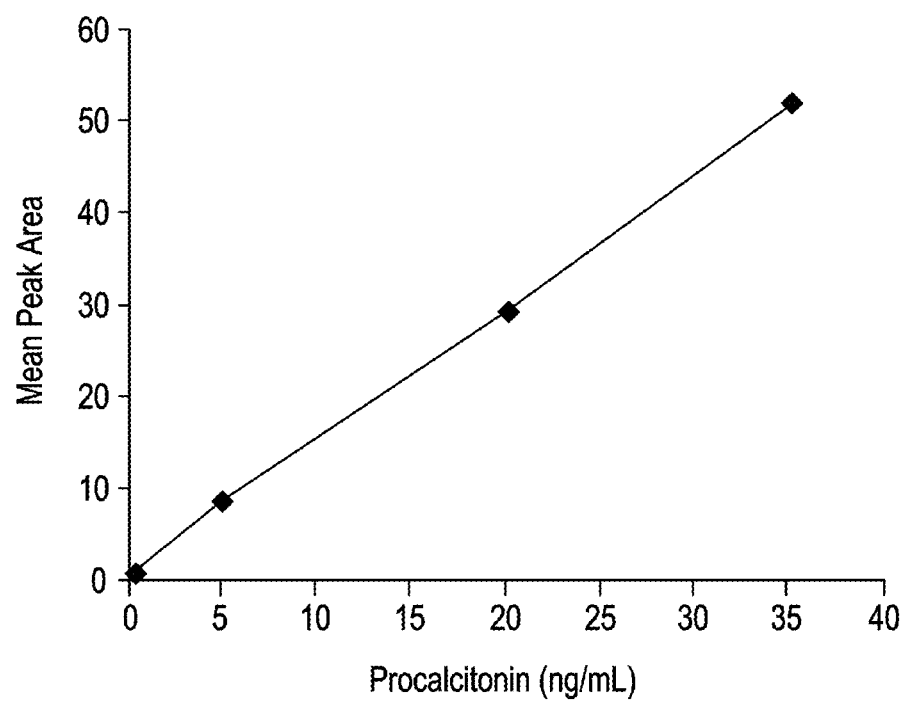
FIG. 13 is a plot of procalcitonin concentration vs. mean peak area using a whole blood sample and a wash.

Miniaturized assay devices having dual reagent cells made of Zeonor (Zeon, Japan) having oxidized dextran on the surface for covalently immobilization of proteins via Schiff base coupling were used. Fluorescently labeled anti-procalcitonin monoclonal antibody was deposited and dried to create a reagent zone. Anti-procalcitonin monoclonal antibody was deposited and dried to create a detection zone. A small amount of Triton X-45 was deposited on the device to increase wettability of the sample for better capillary flow. In this example 25 microliters of whole blood containing procalcitonin was applied to a filter in contact with the sample addition zone of the assay device. Plasma is transferred from the filter into the sample addition zone and then moves by capillary force through the flow path to the wicking zone. The fluid flow was monitored by visual inspection and 10 microliters of a wash fluid containing 0.01 M phosphate buffer, 0.0027 M potassium chloride, 0.137 M sodium chloride, 1% bovine serum albumin and 0.1% triton X-100 was added to the reagent addition zone when the fluid flow front filled 20% of the wicking zone. The assay device was inserted into a fluorescent reader immediately after the wicking zone was determined to be completely filled. The fluorescent signal within the detection zone was measured and the peak area under the response curve was determined for each sample. Whole blood samples were collected fresh from normal donors in lithium heparin tubes. A concentrated serum sample containing 10 ug/mL procalcitonin was added to aliquots of whole blood to create samples containing 0, 0.4, 5, 20 and 35 ng/mL procalcitonin. FIG. 13 plots the mean peak area of five replicate results for each sample versus the procalcitonin concentration. As FIG. 13 demonstrates, using a small sample size (i.e., 25 µL whole blood/10 µL wash) provides satisfactory results over a wide range of analyte concentrations.

Example 4

Figure 14:
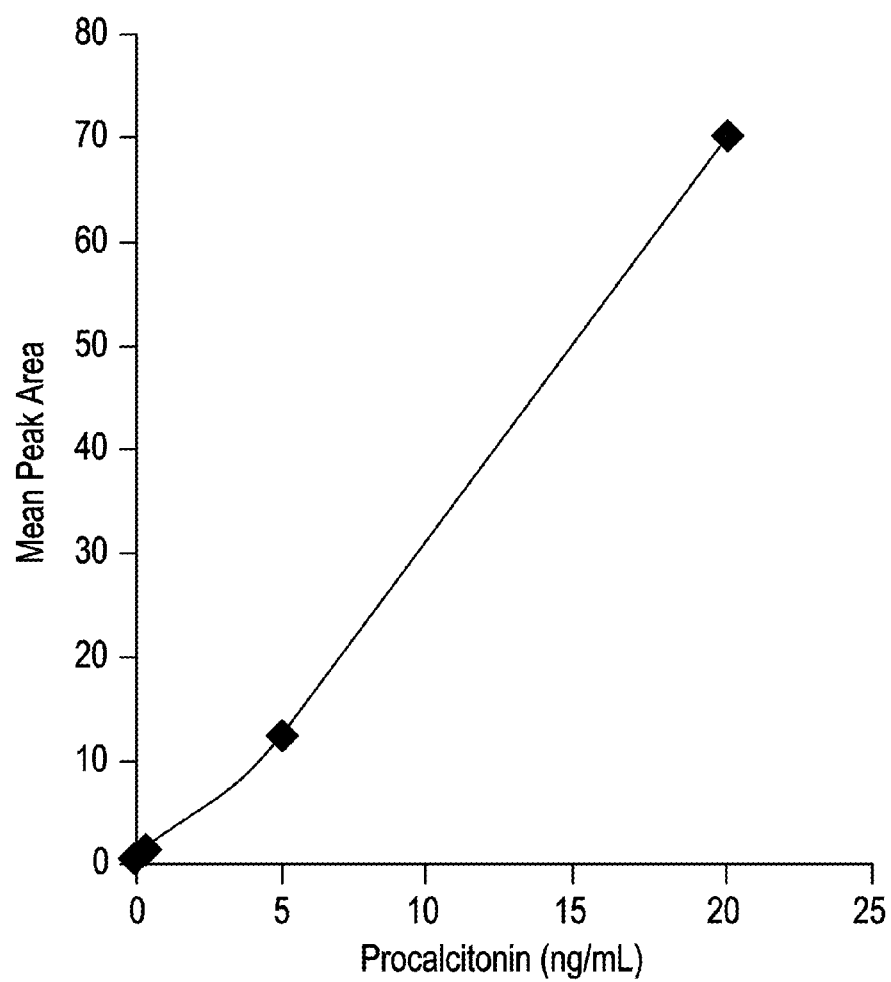
FIG. 14 is a plot of procalcitonin concentration vs. mean peak area using a whole blood sample.

Miniaturized assay devices having dual reagent cells made of Zeonor (Zeon, Japan) having oxidized dextran on the surface for covalently immobilization of proteins via Schiff base coupling were used. Fluorescently labeled anti-procalcitonin monoclonal antibody was deposited and dried to create a reagent zone. Anti-procalcitonin monoclonal antibody was deposited and dried to create a detection zone. A small amount of Triton X-45 was deposited on the device to increase wettability of the sample for better capillary flow. In this example thirty five microliters of whole blood containing procalcitonin was applied to a filter in contact with the sample addition zone of the assay device. Plasma is transferred from the filter into the sample addition zone then moves by capillary force through the flow path to the wicking zone. The fluid flow was monitored by visual inspection and inserted into the fluorescent reader immediately after the wicking zone was determined to be completely filled. The fluorescent signal within the detection zone was measured and the peak area under the response curve was determined for each sample. Whole blood samples were collected fresh from normal donors in EDTA tubes. A concentrated serum sample of 10 ug/mL procalcitonin was added to aliquots of whole blood to create samples containing 0, 0.4, 5, and 20 ng/mL procalcitonin. FIG. 14 plots the mean peak area of three replicate results for each sample versus the procalcitonin concentration. As FIG. 14 demonstrates, using a small sample size (i.e., 35 µL whole blood) provides satisfactory results over a wide range of analyte concentrations.

Example 5

Assay devices made of Zeonor (Zeon, Japan) having oxidized dextran on the surface for covalently immobilization of proteins via Schiff base coupling were used. Fluorescently labeled Anti-iPTH polyclonal antibody was deposited and dried to create a reagent zone. Anti-iPTH polyclonal antibody was deposited and dried to create a detection zone. A small amount of Triton X-45 was deposited on the device to increase wettability of the sample for better capillary flow. A 15 microliter aliquot of iPTH patient sample was added to the sample zone of the device and the capillary action of the micropillar array distributed the sample through the flow channel into the wicking zone. A typical assay time was about 10 minutes. The signal intensities from the fluorescently labeled complexes in the detection zone were recorded in a prototype line-illuminating fluorescence scanner. Table X compares the peak area generated for iPTH with single and twin conjugate cells. The results clearly demonstrate the superiority of multiple reagent cells vs single reaction cells.

| Patient Sample Response (RFU) | | |
|---|---|---|
| Patient samples serum iPTH Conc. (pg/mL) | Single Reagent Cell | Dual Reagent Cells |
| 5.4 | 0.04 | 0.16 |
| 62 | 0.11 | 0.38 |
| 310 | 0.71 | 1.75 |
| 576 | 1.20 | 3.10 |
| 809 | 1.72 | 3.81 |

Additional Embodiments

1. An assay device comprising: a liquid sample zone; a reagent zone downstream and in fluid communication with the sample zone comprising at least two reagent cells containing a reagent material and arranged in the reagent zone such that each reagent cell experiences substantially the same flow conditions of sample from the sample zone, wherein the reagent cells divide the sample flow from the sample zone into multiple flow streams; one or more flow control elements disposed downstream from the reagent zone which combine the multiple flow streams into fewer flow streams; a detection zone in fluid communication with the reagent zone; and a wicking zone in fluid communication with the detection zone having a capacity to receive liquid sample flowing from the detection zone, wherein the sample addition zone, the detection zone and the wicking zone define a fluid flow path.

2. An assay device as disclosed in embodiment 1, wherein the at least two reagent cells are arranged symmetrically in the reagent zone.

3. An assay device as disclosed in embodiment 1, wherein the elements are arranged such that each flow stream is subjected to the same flow resistance.

4. An assay device as disclosed in embodiment 1, wherein the capture zone has a substrate and projections which extend substantially vertically from the substrate, wherein the projections have a height, cross-section and a distance between one another that defines a capillary space between the projections capable of generating capillary flow parallel to the substrate surface.

5. An assay device as disclosed in embodiment 1, wherein the reagent material comprises a labeled reagent material, and the detection zone has capture elements bound thereto.

6. An assay device as disclosed in embodiment 1, wherein the at least two reagent zones comprises three or more reagent zones.

7. An assay device comprising: a liquid sample addition zone; a reagent zone downstream and in fluid communication with the sample addition zone comprising $2^n$ reagent cells, where n is a non-zero, non-negative integer, arranged in the reagent zone such that each reagent cell experiences substantially the same flow conditions of sample from the sample addition zone, wherein the reagent cells divide the sample flow from the sample addition zone into multiple flow streams; flow control elements which separate the reagent cells; one or more flow control elements disposed downstream from the reagent zone which combine the multiple flow streams into fewer flow streams; a detection zone in fluid communication with the reagent zone capable of producing a detectable signal; and a wicking zone in fluid communication with the capture zone having a capacity to receive liquid sample flowing from the capture zone, wherein the sample addition zone, the capture zone and the wicking zone define a fluid flow path.

8. An assay device as disclosed in embodiment 7, wherein the elements are arranged such that each flow stream is subjected to the same flow resistance.

9. An assay device as disclosed in embodiment 7, wherein the capture zone has a substrate and projections which extend substantially vertically from the substrate, wherein the projections have a height, cross-section and a distance between one another that defines a capillary space between the projections capable of generating capillary flow parallel to the substrate surface.

10. An assay device as disclosed in embodiment 7, wherein the detection zone comprises capture elements bound thereto.

11. An assay device as disclosed in embodiment 7, wherein the multiple flow streams are $(2^n) \times 2$ flow streams.

12. An assay device as disclosed in embodiment 7, wherein the multiple flow streams are combined into a single flow stream.

13. An assay device as disclosed in embodiment 7, wherein the reverse bifurcation elements comprises a first stage which combines the multiple flow streams into $2^n$ flow streams.

14. An assay device as disclosed in embodiment 11, further comprising a second stage which receives the $2^n$ flow streams and combines them into $2^{n-1}$ flow streams.

15. An assay device as disclosed in embodiment 1, wherein the width of the flow path through the detection zones is in the range of about 0.5 to 1.2 mm.

16. An assay device as disclosed in embodiment 1, wherein total area of the assay device is $\leq 900$ mm$^2$.

17. An assay device as disclosed in embodiment 16, wherein total area of the assay device is $\leq 700$ mm$^2$.

18. An assay device as disclosed in embodiment 1, wherein the assay device is rectangular and the dimensions of each side are $\leq 30$ mm.

19. An assay device as disclosed in embodiment 18, wherein the assay device is rectangular and the dimensions are approximately 24×28 mm.

20. An assay device as disclosed in embodiment 1, wherein the assay device is capable of using a sample size of $\leq 50$ μl.

21. An assay device as disclosed in embodiment 20, wherein the assay device is capable of using a sample size of $\leq 40$ μl.

22. An assay device as disclosed in embodiment 21, wherein the assay device is capable of using a sample size of $\leq 35$ μl.

23. An assay device as disclosed in embodiment 22, wherein the assay device is capable of using a sample size of $\leq 25$ μl.

24. An assay device as disclosed in embodiment 15, wherein the one or more flow control elements disposed downstream are arranged to provide channel gates for each of the multiple flow streams which constrict the flow of each of the multiple flow streams.

25. An assay device as disclosed in embodiment 24, wherein the reagent cells prior to contact with a flow stream have a width that is at least 2 times, at least 5 times, or at least 10 times the width of the channel gates.

26. An assay device as disclosed in embodiment 24, wherein the flow control elements are arranged such that the center of the channel gates forms a line of symmetry in the direction of flow with the center of its associated reagent cell.

27. An assay device as disclosed in embodiment 26, wherein the flow control elements comprise structures which extend from the base of a substrate from the device and block the flow of sample and the channel gates are formed from discontinuities of the elements.

28. An assay device as disclosed in embodiment 27, wherein the assay device comprises a substrate that includes a channel for containing the reagent zone and the detection zone, and wherein the outermost flow control structures in a direction perpendicular to flow are wall portions of the channel which extend into the channel.

29. An assay device as disclosed in embodiment 27, wherein the sides of the channel are substantially straight in the direction of flow and the outermost flow control structures extend from the sidewalls of the channel and extend into the channel in a direction substantially perpendicular to the channel.

30. An assay device as disclosed in embodiment 7, further comprising elements disposed upstream from the reagent cells which contribute to each reagent cell experiencing substantially the same flow conditions of sample from the sample addition zone.

31. An assay device as disclosed in embodiment 30, wherein the one or more elements disposed upstream comprise one or more flow control elements.

32. An assay device as disclosed in embodiment 30, wherein the one or more elements disposed upstream comprise micropillars having a dimension that is different from the other surrounding micropillars.

33. An assay device as disclosed in embodiment 31, wherein the one or more flow control elements disposed downstream are arranged to provide channel gates which are adapted to constrict the flow of each of the multiple flow streams.

34. An assay device as disclosed in embodiment 33, wherein the flow control elements are arranged such that the center of the channel gates forms a line of symmetry with the center of the reagent cells.

35. An assay device as disclosed in embodiment 34, wherein the elements comprise structures which extend from the base of a substrate from the device and block the flow of sample and the channel gates are formed from discontinuities of the elements.

36. A method of controlling the flow around the reagent zone in an assay device comprising: providing a liquid sample zone; providing a reagent zone upstream and in fluid communication with the sample zone comprising at least two reagent cells arranged in the reagent zone such that each reagent cell experiences substantially the same flow conditions of sample from the sample zone, wherein the reagent cells divide the sample flow from the sample zone into multiple flow streams; providing one or more flow control elements disposed upstream from the reagent zone, arranged to provide channel gates having a width narrower than the reagent cells and which are adapted to constrict the flow from the sample leaving the sample zone; providing one or more flow control elements disposed downstream from the reagent zone which combine the multiple flow streams into fewer flow streams; providing a detection zone in fluid communication with the reagent zone; providing a wicking zone in fluid communication with the capture zone having a capacity to receive liquid sample flowing from the capture zone, wherein the sample zone, the detection zone and the wicking zone define a fluid flow path; adding sample to the sample zone; flowing the sample from the sample zone through the upstream flow channel gates which increase the velocity of the flow; flowing the sample past the reagent zone, whereby the flow has an increased flow rate near the reagent boundary compared to the flow at a distance from the reagent boundary, resulting in a more complete dissolution of the reagent zone; flowing the sample past the downstream flow channel gates, which increases the velocity of the flow and results in a wider reagent plume flowing through the detection zone, as compared to a reagent plume generated by a single reagent cell.

37. A method as disclosed in embodiment 36, wherein the elements are arranged such that each flow stream is subjected to the same flow resistance.

38. A method as disclosed in embodiment 36, wherein the detection zone has a substrate and projections which extend substantially vertically from the substrate, wherein the projections have a height, cross-section and a distance between one another that defines a capillary space between the projections capable of generating capillary flow parallel to the substrate surface.

39. A method as disclosed in embodiment 36, wherein the wider reagent plume extends across the entire width of the detection zone.

40. A method of performing an assay on a liquid sample for the presence or concentration of one or more analyte(s) or control(s), on the assay device according to embodiment 1, comprising: depositing a liquid sample containing the analyte(s) of interest onto a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

Co pending applications entitled "Low Volume Assay Device Having Increased Sensitivity" (Application No. 61/588,758, first named inventor: Phil Hosimer), "Assay Device Having Multiplexing" (Application No. 61/588,779, first named inventor: Sue Danielson), "Assay Device Having Uniform Flow Around Corners" (Application No. 61/588,745, first named inventor James Kanaley), "Controlling Fluid Flow Through An Assay Device" (Application No. 61/588,772, first named inventor James Kanaley), and "Assay Device Having Controllable Sample Size" (Application No. 61/588,899, first named inventor, Ed Scalice), all filed Jan. 20, 2012 and all incorporated by reference in their entireties.

What is claimed is:
1. An assay device comprising:
  a liquid sample addition zone;
  a reagent zone downstream and in fluid communication with the liquid sample addition zone comprising at least two reagent cells, each reagent cell containing a reagent material and arranged in the reagent zone such that each reagent cell experiences substantially the same flow conditions of sample from the liquid sample addition zone, wherein the at least two reagent cells are separated from one another within the reagent zone and in which the reagent zone includes a separator for separating the at least two reagent cells, wherein a plurality of upstream flow control elements are disposed that form gates aligned with each reagent cell that divide the sample flow from the liquid sample addition zone into multiple flow streams corresponding to each reagent cell and in which the reagent material in each reagent cell is dissolved by moving liquid sample and produces a detectable plume;

flow control elements disposed downstream from the reagent zone, forming gates aligned with the reagent cells which combine the multiple flow streams into fewer flow streams exiting the reagent zone;

a detection zone in fluid communication with the reagent zone wherein the downstream flow control elements merge the fewer flow streams into the detection zone; and a wicking zone in fluid communication with the detection zone having a capacity to receive liquid sample flowing from the detection zone, wherein the liquid sample addition zone, the detection zone and the wicking zone define a fluid flow path.

2. An assay device as claimed in claim 1, wherein the at least two reagent cells are arranged symmetrically in the reagent zone.

3. An assay device as claimed in claim 1, wherein the upstream and downstream flow control elements are arranged such that each flow stream is subjected to the same flow resistance.

4. An assay device as claimed in claim 1, wherein the device further comprises a substrate and having projections which extend substantially vertically from the substrate, wherein the projections have a height, cross-section and a distance between one another that defines a capillary space between the projections capable of generating capillary flow parallel to the substrate surface and along the defined fluid flow path.

5. An assay device as claimed in claim 1, wherein the reagent material comprises a labeled reagent material, and the detection zone has capture elements bound thereto.

6. An assay device as claimed in claim 1, wherein the at least two reagent zones comprises three or more reagent zones.

7. An assay device comprising:
a liquid sample addition zone;
a reagent zone downstream and in fluid communication with the liquid sample addition zone comprising $2^n$ reagent cells, where n is a non-zero, non-negative integer, arranged in the reagent zone such that each reagent cell experiences substantially the same flow conditions of sample from the liquid sample addition zone, wherein the reagent cells divide the sample flow from the liquid sample addition zone into multiple flow streams and in which each of the reagent cells contain a reagent material that is dissolved upon contact with a flowing sample added to the sample addition area in which the dissolved reagent material reacts to produce a detectable plume;
flow control elements including separators disposed within the reagent zone which separate the reagent cells from one another within the reagent zone to create the multiple flow streams;
in which one or more of the flow control elements are disposed downstream from the reagent zone which combine the multiple flow streams into fewer flow streams which exit the reagent zone;
a detection zone in fluid communication with the reagent zone that receives the fewer flow streams exiting the reagent zone, the detection zone being defined by a single channel having capture elements; and
a wicking zone in fluid communication with the capture detection zone having a capacity to receive liquid sample flowing from the capture detection zone, wherein the sample addition zone, the capture detection zone and the wicking zone define a fluid flow path.

8. An assay device as claimed in claim 7, wherein the flow control elements are arranged such that each flow stream is subjected to the same flow resistance.

9. An assay device as claimed in claim 7, wherein the multiple flow streams are $(2^n) \times 2$ flow streams.

10. An assay device as claimed in claim 7, wherein the multiple flow streams are combined into a single flow stream when entering the detection zone from the reagent zone.

11. An assay device as claimed in claim 7, wherein the flow control elements downstream of the reagent cells comprises a first stage which combines the multiple flow streams into $2^n$ flow streams prior to exiting the reagent zone.

12. An assay device as claimed in claim 11, further comprising a second stage of flow control elements downstream of the first stage of flow control elements which receives the $2^n$ flow streams and combines them into $2^{n-1}$ flow streams.

13. An assay device as claimed in claim 7, wherein the one or more flow control elements disposed downstream are arranged to provide channel gates for each of the multiple flow streams which constrict the flow of each of the multiple flow streams.

14. An assay device as claimed in claim 13, wherein the flow control elements comprise structures which extend from the base of a substrate from the device and block the flow of sample and the channel gates are formed from discontinuities of the elements.

15. An assay device as claimed in claim 14, wherein the assay device comprises a substrate that includes a channel for containing the reagent zone and the detection zone, and wherein the outermost flow control elements are wall portions of the channel which extend into and narrow the channel.

16. An assay device as claimed in claim 15, wherein the sides of the channel are substantially straight in the direction of flow and the outermost flow control elements extend from the sidewalls of the channel and extend into and narrow the channel.

17. An assay device as claimed in claim 16, further comprising flow control elements disposed upstream from the reagent cells which contribute to each reagent cell experiencing substantially the same flow conditions of sample from the sample addition zone, each of the upstream flow control elements creating gates aligned with the reagent cells.

18. An assay device as claimed in claim 17, wherein the flow control elements which separate the reagent cells and the flow control elements disposed upstream and downstream from the reagent cells are in the shape of an hourglass structure.

19. An assay device as claimed in claim 7, further comprising flow control elements disposed upstream from the reagent cells which contribute to each reagent cell experiencing substantially the same flow conditions of sample from the sample addition zone.

20. A method of controlling the flow around the reagent zone in an assay device comprising:

providing a liquid sample zone;

providing a reagent zone upstream and in fluid communication with the sample zone, the reagent zone comprising at least two reagent cells arranged in the reagent zone such that each reagent cell experiences substantially the same flow conditions of sample from the liquid sample zone, each reagent cell containing a reagent material capable of producing a detectable reagent plume when acted upon by liquid sample moved by capillary action from the liquid sample zone;

providing one or more flow control elements upstream from the reagent zone, the one or more upstream flow control elements being arranged to provide channel gates having a width narrower than the reagent cells and which are adapted to constrict the flow from the sample leaving the liquid sample zone wherein the flowing sample is divided into multiple flow streams, each flow stream being configured to flow relative to a corresponding reagent cell, each of the reagent cells being separated within the reagent zone by a flow control separator;

providing one or more flow control elements disposed downstream from the reagent zone which combine the multiple flow streams into fewer flow streams exiting the reagent zone;

providing a detection zone in fluid communication with the reagent zone that receives the fewer flow streams exiting the reagent zone;

providing a wicking zone in fluid communication with the detection zone having a capacity to receive liquid sample flowing from the detection zone, wherein the liquid sample zone, the detection zone and the wicking zone define a fluid flow path;

adding sample to the liquid sample zone;

flowing the sample from the liquid sample zone through the upstream flow channel gates which increase the velocity of the flow;

flowing the sample past the separated reagent cells in the reagent zone along the multiple flow paths, whereby the flow has a larger flow rate near the reagent boundary compared to the flow at a distance from the reagent boundary, resulting in a more complete dissolution of each reagent cell;

flowing the sample past the downstream flow channel gates, which results in a wider reagent plume flowing into and through the detection zone, as compared to a reagent plume generated by a single reagent cell.

21. An method as claimed in claim 20, wherein the elements are arranged such that each flow stream is subjected to the same flow resistance.

22. A method as claimed in claim 20, wherein the wider reagent plume extends across the entire width of the detection zone.

23. A method of performing an assay on a liquid sample for the presence or concentration of one or more analyte(s) or control(s), on the assay device according to claim 1, comprising:

depositing a liquid sample containing the analyte(s) of interest onto a sample addition zone of the assay device;

moving the sample by capillary action through a fluid flow path into a reagent zone where the sample dissolves one or more reagents;

flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

* * * * *

UNITED STATES PATENT AND TRADEMARK OFFICE
CERTIFICATE OF CORRECTION

PATENT NO. : 9,689,870 B2  
APPLICATION NO. : 14/578745  
DATED : June 27, 2017  
INVENTOR(S) : Zhong Ding Page 1 of 1

It is certified that error appears in the above-identified patent and that said Letters Patent is hereby corrected as shown below:

Claim 4:
Column 21
Line 35, please change "device further comprises a substrate and having projections" to --device further comprises a substrate having projections--

Claim 7:
Column 22
Line 9, please change "a wicking zone in fluid communication with the capture" to --a wicking zone in fluid communication with the--

Claim 7:
Column 22
Line 11, please change "sample flowing from the capture detection zone," to --sample flowing from the detection zone,--

Claim 7:
Column 22
Line 11, please change "wherein the sample addition zone, the capture detection" to --wherein the sample addition zone, the detection--

Signed and Sealed this
Twelfth Day of June, 2018

Andrei Iancu
*Director of the United States Patent and Trademark Office*